United States Patent [19]

Blume et al.

[11] Patent Number: 5,155,237
[45] Date of Patent: Oct. 13, 1992

[54] PREPARATION OF 2,2-DIHYDROCARBYL-3-PROPIOLACTONES

[75] Inventors: Roe C. Blume; Lewis E. Manring, both of Wilmington, Del.

[73] Assignee: E. I. Du Pont de Nemours and Company, Wilmington, Del.

[21] Appl. No.: 644,388

[22] Filed: Jan. 22, 1991

[51] Int. Cl.[5] .......................................... C07D 305/12
[52] U.S. Cl. .................................... 549/328; 528/417
[58] Field of Search ......................................... 549/328

[56] References Cited

U.S. PATENT DOCUMENTS 3,751,435 8/1973 van der Ven ........................ 549/328
4,550,181 10/1985 Murib et al. ......................... 549/326

FOREIGN PATENT DOCUMENTS 4830067 9/1973 Japan.

OTHER PUBLICATIONS

T. L. James et al., J. Am. Chem. Soc., vol. 91, pp. 7743-7746 (1969).
L. E. Manring et al., Macromolecules, vol. 23, pp. 1902-1907 (1990).

Primary Examiner—Jane T. Fan

[57] ABSTRACT

2,2-Dihydrocarbyl-3-propiolactones are prepared by the thermolysis at 175° C. to 350° C. of low molecular weight (oligomeric) poly(3-hydroxy-2,2-dihydrocarbyl-propionic acid) that contains carboxyl ends groups, in the presence of alkali metal, ammonium or phosphonium cations. The propiolactones may be polymerized to high molecular weight polymers.

20 Claims, 1 Drawing Sheet

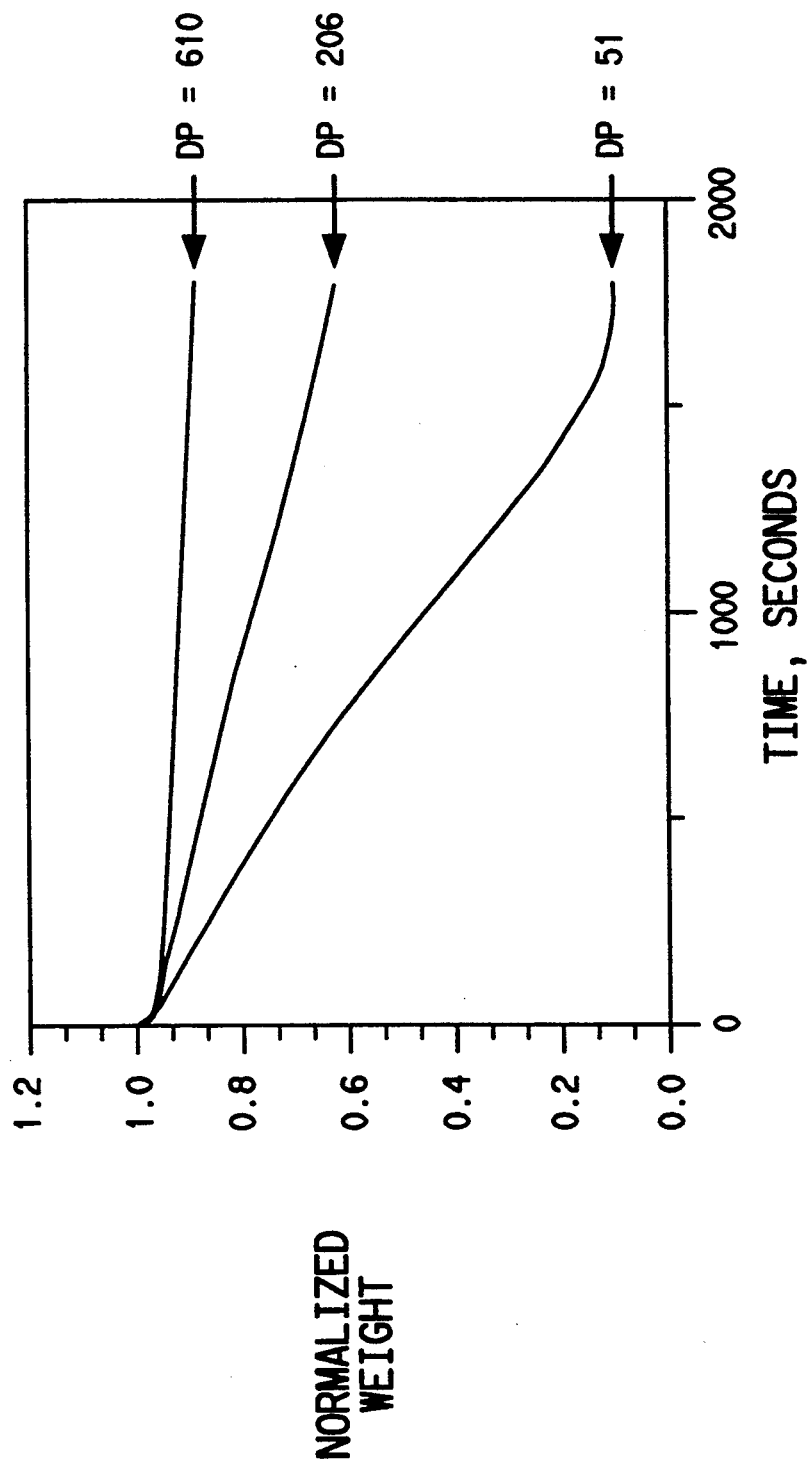
FIGURE

PREPARATION OF 2,2-DIHYDROCARBYL-3-PROPIOLACTONES

BACKGROUND OF THE INVENTION

1. FIELD OF THE INVENTION

The preparation of 2,2-dihydrocarbyl-3-propiolactones by thermolysis of oligomeric 3-hydroxy-2,2-dihydrocarbylpropionic acid that contains a carboxyl end, in the presence of selected cationic catalysts is disclosed.

2. TECHNICAL BACKGROUND

The general concept of heating the polyesters of hydroxy acids to prepare lactones, and particularly caprolactones (forming seven-membered rings) has been known for a long time, see for example W. H. Carothers, et. al., J. Am. Chem. Soc., vol. 54, p. 761–772 (1932) and references therein. A more recent reference is, for example, U.S. Pat. No. 4,550,181, in which polycaprolactone is heated in the presence of water and a hydrogen halide to form caprolactone. However, preparation of lactones with four ring atoms, 3-propiolactones, is more difficult by these methods because of the propiolactone's greater tendency to undergo thermal degradation [see for example T. L. James and C. A. Wellington, J. Am. Chem. Soc., vol. 91, p. 7743–7746 (1969)].

Japanese Patent Application 48-30067 describes the preparation of episilon-caprolactone by the thermolysis of a polycaprolactone oligomer having a degree of polymerization of 2 to about 20. However, the process is carried out with the ester of the oligomeric caprolactone or in the presence of an alcohol. The application states that it is preferable "that the carboxyl groups derived from these free acids be esterified" (from the translation). Thus free carboxyl groups are undesirable according to this Japanese Application.

U.S. Pat. No. 3,751,435 describes the thermolysis above 245° C. of poly(pivalolactone) in the presence of certain basic substances or neutral salts to give pivalolactone (2,2-dimethyl-3-propiolactone). No mention is made of the degree of polymerization of the poly(pivalolactone) used or the end groups it contains.

I. Luderwald, Makromol. Chem., vol. 182, p. 867–871 (1981), reports the thermolysis of poly(pivalolactone) in the presence of certain metal salts. No mention is made of the original degree of polymerization, or the end groups of the poly(pivalolactone) used.

L. E. Manring, et. al., Macromolecules, vol. 23, p. 1902–1907 (1990), reports that oligomers of poly(2-methyl-2-n-propyl-3-propiolactone) containing carboxyl ends, in the presence of certain cations, thermolyze faster than higher molecular weight polymers, or polymers that do not contain carboxyl ends.

It is an object of this invention to provide a method for the preparation of 2,2-dihydrocarbyl-3-propiolactones by the thermolysis of oligomers of the corresponding hydroxy acids having a relatively low degree of polymerization, and which contain carboxyl(ate) ends, in the presence of certain cations. This combination of conditions allows the use of lower temperatures and/or shorter residence times for the thermolysis, which in turn results in superior yields of the desired propiolactone.

SUMMARY OF THE INVENTION

This invention concerns a process for the preparation of 2,2-dihydrocarbyl-3-propiolactones, comprising, heating at a temperature about 175° C. to about 350° C., (a) a mixture of

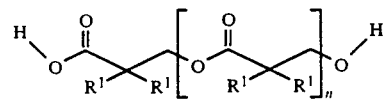

with a compound of the formula MY; or (b) an oligomer of the formula

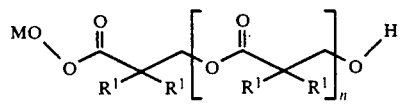

wherein:

each $R^1$ is independently hydrocarbyl;

n is 2 to about 200;

M is a cation selected from the group consisting of alkali metal cations, $R^2_4P^+$, and $R^2_4N^+$;

Y is an anion whose conjugate acid has a pKa of more than about 2 in water; and each $R^2$ is independently hydrocarbyl.

Also provided is a process comprising the additional step of polymerizing the 2,2-dihydrocarbyl-3-propiolactone that is formed.

DETAILS OF THE INVENTION

The process described herein involves the thermolysis of an oligomer of a 3-hydroxy-2,2-dihydrocarbylpropionic acid to form the corresponding lactone. The oligomer may be made by the condensation polymerization of the propionic acid, a process known to those skilled in the art. For instance, see Experiment 1 herein, G. Odian, Principles of Polymerization, John Wiley & Sons, New York, 1981, p. 102–105, and F. W. Billmeyer, Jr., Textbook of Polymer Science, Third Ed., John Wiley & Sons, New York, 1984, p. 26–40, both of which are hereby included by reference. Some processes for making the oligomer, particularly the condensation of the hydroxy acid, may give some cyclic low oligomers as products. These cyclic compounds do not undergo the thermolysis readily. However, they may be volatile enough to be recovered in the thermolysis as a vapor along with the propiolactone. When separated from the propiolactone, they may be recycled back to the corresponding hydroxy acid.

The two hydrocarbyl groups ($R^1$) (originally in the two position of the monomer) are independently chosen. It is preferred if each group $R^1$ independently contains 1 to about 8 carbon atoms. It is also preferred if each $R^1$ is independently phenyl or alkyl containing 1 to about 8 carbon atoms, and more preferred if each $R^1$ is independently an alkyl group containing 1 to 4 carbon atoms. Especially preferred combinations of the groups $R^1$ are dimethyl and methyl with n-propyl.

The degree of polymerization (sometimes abbreviated herein as DP), as used herein, means the average number of monomer units in the oligomer molecule. Thus the degree of polymerization equals n+1. It is preferred if n is 5 to about 100, and more preferred if n is about 10 to about 75.

The cation M is added as a compound, in which conjugate acid of the anion Y has a pKa of about 2 or more in water. Useful anions Y include, but are not limited to, bicarbonate, acetate, formate, benzoate, carbonate, hydroxide, and phenoxide. [Compounds that contain relatively basic anions (the pKa of its conjugate acid is about 7 or more), such as cesium hydroxide, may actually cleave the oligomer chains randomly instead of at the ends, but the effect is limited, since on the first cleavage, the anion is destroyed. The degree of polymerization of the oligomer used in the instant process shall be the degree of polymerization after such cleavage.] Alternatively, the cation may be present as the salt of the carboxyl end group of the oligomer. It is believed that if the cation is added as the compound MY, during the process, at least some of the cation is converted to the salt of the carboxyl end groups present.

Although only a catalytically effective amount of cation need be present, it is preferred if the molar amount of cation present is in at least approximately equimolar amounts to the amount of carboxyl end group present, and if added as the compound MY, it is more preferred if about 1% to about 30% excess M on a molar basis, compared to carboxyl groups, be present.

The alkali metal (lithium, sodium, potassium and cesium) cations are preferred for M, potassium and cesium are more preferred, and cesium cation is especially preferred. It is believed the cation $R^2_4P^+$ is relatively unstable at process temperatures, and may catalyze the decomposition of the propiolactone product. These problems are believed to be even more severe with $R^2_4N^+$, although in both cases, the desired product is still obtained. Preferred $R^2$ groups are alkyl groups containing 1 to 6 carbon atoms.

In order to minimize degradation of the desired product, the process should be carried out at as low a temperature as possible commensurate with obtaining a reasonable reaction rate. The preferred process temperature is about 190° C. to about 275° C., and a more preferred temperature is about 200° C. to about 240° C. Even if temperatures at the higher end of the range are used in the process, the improvement in reaction rate afforded by the conditions enumerated herein provide higher product yields, due to lower residence times. (These concerns have also been addressed in U.S. Pat. No. 3,751,435, which is hereby incorporated by reference).

Also important to minimize product degradation is removal of the product from the hot reaction zone as rapidly as possible. In order to do this, the process is preferably carried out under vacuum, to help effect rapid removal of the desired propiolactone from the reaction matrix. The use of certain types of apparatus, such as so-called thin or wiped film reactors, also facilitates rapid reaction and removal of the product, and is preferred. Such equipment is known to those skilled in the art, see for example U.S. Pat. No. 4,556,324, which is hereby included by reference.

Normally the product propiolactone will exit the process (thermolysis) as a vapor, particularly if a vacuum is applied. The vapor may be condensed and cooled, and if higher purity is desired, the product may be distilled (or recrystallized in the case of solids).

The above described process may also comprise the further step of polymerizing the 2,2-dihydrocarbyl-3-propiolactone to the corresponding polyester, which is a polymer comprising the repeat unit

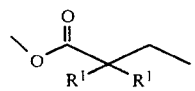

Such polymerizations are known to those skilled in the art, for instance, see Example 2 herein, and D. B. Johns, et. al., in K. J. Ivin and T. Saegusa, Ring-Opening Polymerization, Vol. 1, Elsevier Applied Science Publishers, Ltd., Barking, Essex, England, 1984, all of Chap. 7, but particularly p. 468–500; all of Chap. 7 is hereby incorporated by reference.

In the following examples, the hydroxy acid, oligomer and product propiolactone are substituted in the 2 position with a methyl and an n-propyl group, so that the propiolactone obtained is 2-methyl-2-n-propyl-3-propiolactone, which is sometimes abbreviated MP in the Examples.

DESCRIPTION OF THE DRAWING

The FIGURE shows relative mass loss with time for three samples described in Example 3.

EXPERIMENT 1

To a 1L stirred stainless steel autoclave was added 684 g of 2-methyl-2propyl-3-hydroxypropanoic acid. With stirring and a slow $N_2$ purge, the vessel was heated as follows: room temperature to 180° C. for 4 hours; to 200° C. for 4 hours. The vessel was cooled to 100° C. and 5 ml of tetraisopropyl titanate was added. With stirring and a slow $N_2$ purge, the vessel was heated again as follows: 100° C. to 210° C. for 4 hours; to 220° C. for 4 hours; to 230° C. for 24 hours. Gel permeation chromatography of the resulting oligomer indicated it had a DP ~16. HPLC analysis indicates that it contains 12–15% cyclic oligomers.

EXAMPLE 1

Solid oligomer from Experiment 1 (27 g) and cesium acetate (1 g) were mixed by pulverizing them in a blender. The resulting fine powder was dried in a 200 ml round bottom flask at 0.5 mmHg for 72 hours.

A series of experiments were done by placing 1 g of the mixture in a 1L flask, which was placed in a kugelrohr (Aldrich Chemical Co., Model #Z101046-3) with a 500 ml receiving flask. A dry ice/acetone cooled trap was placed after the 500 ml receiver to collect material more volatile than MP. The kugelrohr was heated from room temperature to the desired temperature (Table 1) over a ½ hour period and then held at the desired temperature for the time noted in Table 1.

EXAMPLE 2

A sample of oligomer was prepared by ring opening polymerization (rather than condensation as described in Experiment 1) to insure the initial absence of cyclic oligomers. Polymerization was initiated by tetrabutylammonium 3-hydroxy-2-methyl-2-propyl propanoate in refluxing tetrahydrofuran. Initiator solutions were prepared by the addition of equimolar amounts of tetrabutylammonium hydroxide and 3-hydroxy-2-methyl-2-propyl propanoic acid to toluene followed by azeotropic removal of the methanol and water. The final volume was adjusted to give a 0.2M solution of initiator in toluene. Polymerization was carried out as follows. To a 250 ml RB flask was added 100 ml tetrahydrofuran, 15.4 g (0.12 moles) 2-methyl-2-propyl-3-propiolactone and 20 ml of 0.2M initiator. The solution was heated at reflux (~30 minutes) until no lactone was detected by IR (1834 cm$^{-}$). The solution was evaporated to dryness in a nitrogen stream yielding 15.45 g solid. The tetrabutylammonium carboxylate end groups were exchanged with excess acetic acid in THF.

Solid oligomer (15 g) and cesium acetate (0.48 g) were mixed and dried as described in Example 1.

A 1 g sample of the mixture was heated in a kugelrohr at 220° C. for 15 minutes as described in Example 1. Only MP (no cyclic trimer) was collected in the receiver. The observed yield of 0.08 g was ~85% of theoretical.

EXAMPLE 3

Effect of DP on the Relative Rate of Thermolysis

To oligomer samples, prepared as in Example 2, of various molecular weights (0.100 g dissolved in 1 ml methylene chloride) was added equal amounts of cesium acetate (0.100 ml of a 0.2M solution in methanol). The solvents were removed under vacuum. A ~5 mg sample was heated at 5° C./min and the temperature of peak weight loss (first derivative of mass loss) noted. The weight loss is due to conversion of oligomer to MP. The results are shown in Table 2. With cesium acetate catalyst, the thermolysis occurs at a lower temperature for lower DP oligomer. The results in Table 2 confirm that methyl ester terminated oligomer undergoes conversion to MP at a higher temperature than a carboxyl terminated oligomer.

TABLE 1

| Set Temperature | Time at set temperature | Mass left in 1 L flask | Mass in Receiver (% MP/% trimer) | Mass in Trap |
|---|---|---|---|---|
| 200° C. | 60 min | 0.43 g | 0.45 g 92/7 | 0.06 g |
| 200° C. | 10 min | 0.31 g | 0.55 g 91/8 | 0.08 g |
| 230° C. | 10 min | 0.16 g | 0.61 g 93/6 | 0.03 g |
| 240° C. | 30 min | 0.17 g | 0.63 g 97/3 | 0.08 g |

TABLE 2

| DP | Temperature °C. |
|---|---|
| 50 | 288 |
| 100 | 297 |
| 200 | 300 |
| 500 | 315 |
| 5330 | 320 |
| 50* | 315 |

*End groups are methyl ester

Three samples were prepared using different molecular weight oligomer, made as in Example 2. Sample 1; 289 mg of DP=610 and $3.7 \times 10^{-6}$ moles of tetrabutylphosphonium acetate (one equivalent per polymer chain equivalent) were dissolved in 4 ml $CH_2Cl_2$. The solvent was removed under reduced pressure. Sample 2; 293 mg of DP=206 and $1.1 \times 10^{-5}$ moles of tetrabutylphosphonium acetate (one equivalent per polymer chain equivalent) were dissolved in 4 ml $CH_2C_2$. The solvent was removed under reduced pressure. Sample 3; 242 mg of $DP_o$=51 and $3.7 \times 10^{-5}$ moles of tetrabutylphosphonium acetate (one equivalent per polymer chain equivalent) were dissolved in 4 ml $CH_2Cl_2$. The solvent was removed under reduced pressure. Each sample (~5 mg) was heated to 200° C. and mass loss monitored. The FIGURE shows relative mass loss with time for each sample.

Eighteen mg of sample 1 was placed in a reaction tube which was connected to a trap by 1/16-inch diameter stainless steel tubing. With $N_2$ flowing through the reaction tube and trap, the reaction tube was heated to 230° C. while the trap was cooled in liquid $N_2$. After 1 hour heating, the material in the reaction tube had mostly disappeared and the trap contained predominantly MP.

EXAMPLE 4

A 27.0 g sample of the solid oligomer from Experiment 1 was ground in a blender with 1.0 g cesium acetate, then dried overnight at high vacuum. This mixture was pressed to a 13 mm pellet in a mold and placed in the feed hopper of a batch thin film reactor (diagram attached) constructed according to the principles of U.S. Pat. No. 4,556,324 except that the rotors of the batch reactor were arranged at the same angular orientation rather than in the sawtooth stepped helix required in the continuous model.

The reaction was then purged with nitrogen, evacuated to 0.5 mm Hg and heated to 275° C. The reaction was run for 17 min during which time the pressure rose to 2 mm then fell, stabilizing at about 0.9 mm. The reactor was then cooled and opened. Product (10.7 g) was recovered from Trap 1 which had been cooled with solid carbon dioxide. Nmr analysis indicated that it was composed of 38% 2-methyl-2-propyl-3-propiolactone and 58% 2-methyl-1-pentene.

EXAMPLE 5

In a bottle with 10 cm diameter × 10 cm cylindrical wall and 24 × 40 mm standard taper outlet was placed ten 95 mm × 10 mm diameter glass rods and 4.0 g oligomer of Experiment 1 which had been ground with 0.12 g cesium acetate. The bottle was placed in a standard "Kugelrohr" heater (Aldrich #Z13196-2) and assembled via standard taper joints to a 500 ml single bulb received flask cooled with ice, thence through a reciprocating drive (to rotate the Kugelrohr through a 180° angle) to a solid $CO_2$ cooled trap. The apparatus was evacuated to 0.15 mm Hg and heated to 220° C. for 1 hr. There was collected in the single bulb receiving flask 2.14 g 2-methyl-2-propyl-3-propiolactone, 96.5% as assayed by gc (Hewlett Packard 5890 Series II gas chromatograph with flame ionization detector and equipped with a J&W Scientific Co. #122-1031 30M silica capillary column, an HP7673 automatic injector and HP3396 Series II integrator). There was also collected in the trap 0.44 g product consisting of 55.2% 2-methyl-1-pentene and 42.2% 2-methyl-2-propyl-3-propiolactone.

Although preferred embodiments of the invention have been described hereinabove, it is to be understood that there is no intention to limit the invention to the precise constructions herein disclosed, and it is to be further understood that the right is reserved to all changes coming within the scope of the invention as defined by the appended claims.

What is claimed is:

1. A process for the preparation of 2,2-dihydrocarbyl-3-propiolactones, comprising, heating at a temperature about 175° C. to about 350° C.,
   (a) a mixture of

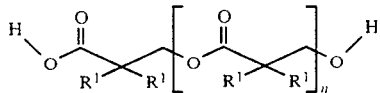

with a compound of the formula MY; or
(b) an oligomer of the formula

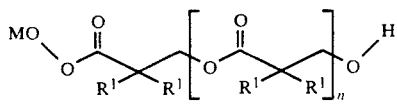

wherein
each $R^1$ is independently hydrocarbyl;
n is 2 to about 200;
M is a cation selected from the group consisting of alkali metal cations, $R^2{}_4P^+$, and $R^2{}_4N^+$;
Y is an anion whose conjugate acid has a pKa of more than about 2 in water; and
each $R^2$ is independently hydrocarbyl.

2. The process as recited in claim 1 wherein each $R^1$ independently contains 1 to about 8 carbon atoms.

3. The process as recited in claim 1 wherein each $R^1$ is independently phenyl or an alkyl group containing 1 to about 8 carbon atoms.

4. The process as recited in claim 3 wherein each $R^1$ is independently an alkyl group containing 1 to 4 carbon atoms.

5. The process as recited in claim 1 wherein said M is an alkali metal cation.

6. The process as recited in claim 5 wherein said M is potassium or cesium.

7. The process as recited in claim 6 wherein said M is cesium.

8. The process as recited in claim 2 wherein said M is an alkali metal cation.

9. The process as recited in claim 4 wherein said M is an alkali metal cation.

10. The process as recited in claim 9 wherein said M is cesium.

11. The process as recited in claim 1 wherein said n is 5 to about 100.

12. The process as recited in claim 11 wherein said n is about 10 to about 75.

13. The process as recited in claim 8 wherein said n is 5 to about 100.

14. The process as recited in claim 9 wherein said n is 5 to about 100.

15. The process as recited in claim 1 wherein said temperature is about 190° C. to about 275° C.

16. The process as recited in claim 15 wherein said temperature is about 200° C. to about 240° C.

17. The process as recited in claim 14 wherein said temperature is about 190° C. to about 275° C.

18. The process as recited in claim 1 wherein said cation is present in at least approximately equimolar amounts with the carboxyl end group.

19. The process as recited in claim 17 wherein said cation is present in at least approximately equimolar amounts with the carboxyl end group.

20. The process as recited in claim 1 wherein each $R^2$ group is independently an alkyl group containing 1 to 6 carbon atoms.

* * * * *